(12) United States Patent
Thompson-Nauman et al.

(10) Patent No.: US 8,346,373 B2
(45) Date of Patent: Jan. 1, 2013

(54) METHOD AND APPARATUS FOR DELIVERING A LEAD TO A HEART

(75) Inventors: Amy E. Thompson-Nauman, Coon Rapids, MN (US); Melissa G. Tanner Christie, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 401 days.

(21) Appl. No.: 12/853,390

(22) Filed: Aug. 10, 2010

(65) Prior Publication Data

US 2012/0035584 A1 Feb. 9, 2012

Related U.S. Application Data

(60) Provisional application No. 61/370,129, filed on Aug. 3, 2010.

(51) Int. Cl.
*A61N 1/02* (2006.01)
*A61B 18/02* (2006.01)

(52) U.S. Cl. ............................. 607/122; 606/20; 606/22

(58) Field of Classification Search ................ 607/115, 607/122; 600/585; 606/20–26
See application file for complete search history.

(56) References Cited

U.S. PATENT DOCUMENTS

| | | | |
|---|---|---|---|
| 3,228,400 A | 1/1966 | Armao | |
| 3,289,749 A | 12/1966 | Crump | |
| 3,512,531 A | 5/1970 | Crump et al. | |
| 3,575,176 A | 4/1971 | Crump et al. | |
| 3,737,579 A | 6/1973 | Bolduc | |
| 3,827,436 A | 8/1974 | Stumpf et al. | |
| 3,875,947 A | 4/1975 | Jula et al. | |
| 3,910,278 A | 10/1975 | Crandell et al. | |
| 3,951,152 A | 4/1976 | Crandell et al. | |
| 3,993,075 A | 11/1976 | Lisenbee et al. | |
| 4,146,037 A | 3/1979 | Flynn et al. | |
| 4,280,510 A | 7/1981 | O'Neill | |
| 4,282,886 A | 8/1981 | King | |
| 4,602,628 A | 7/1986 | Allen, Jr. | |
| 4,723,940 A | 2/1988 | Wiegerinck | |
| 4,991,578 A | 2/1991 | Cohen | |
| 5,336,252 A | 8/1994 | Cohen | |
| 5,443,492 A | 8/1995 | Stokes et al. | |
| 5,827,216 A | 10/1998 | Igo et al. | |
| 5,871,532 A | 2/1999 | Schroeppel | |
| 5,904,711 A | 5/1999 | Flom et al. | |
| 5,931,810 A | 8/1999 | Grabek | |
| 5,972,013 A | 10/1999 | Schmidt | |
| 6,231,518 B1 | 5/2001 | Grabek et al. | |
| 6,592,552 B1 | 7/2003 | Schmidt | |
| 6,613,062 B1 | 9/2003 | Leckrone et al. | |
| 6,890,295 B2 | 5/2005 | Michels et al. | |

(Continued)

FOREIGN PATENT DOCUMENTS

EP 1430848 A1 6/2004

(Continued)

*Primary Examiner* — Tammie K Heller

(57) ABSTRACT

A method and apparatus for creating and accessing an anatomic space between a heart and a pericardial sac. The apparatus includes a catheter having a cryoadhesion member situated on the distal tip of the catheter. The cryoadhesion member is utilized to adhere to the pericardial sac and to retract the sac to create a tent like structure. The catheter allows introduction of an instrument to access the pericardial sac by puncture. The access to the pericardial sac allows delivery of a device, a drug, a biologic or other substance to the heart or the space around the heart.

15 Claims, 3 Drawing Sheets

U.S. PATENT DOCUMENTS

| | | |
|---|---|---|
| 7,146,225 B2 | 12/2006 | Guenst et al. |
| 7,162,309 B2 | 1/2007 | Laske et al. |
| 7,186,214 B2 | 3/2007 | Ness |
| 7,207,988 B2 | 4/2007 | Leckrone et al. |
| 7,270,669 B1 | 9/2007 | Sra |
| 7,610,104 B2 | 10/2009 | Kaplan et al. |
| 7,620,458 B2 | 11/2009 | Friedman et al. |
| 7,625,369 B2 | 12/2009 | Abboud et al. |
| 2003/0074041 A1 | 4/2003 | Parry et al. |
| 2003/0093104 A1 | 5/2003 | Bonner et al. |
| 2003/0212446 A1 | 11/2003 | Kaplan et al. |
| 2004/0199236 A1 | 10/2004 | Laske et al. |
| 2006/0247672 A1 | 11/2006 | Vidlund et al. |
| 2009/0187074 A1* | 7/2009 | Saadat et al. .................. 600/114 |
| 2012/0095434 A1* | 4/2012 | Fung et al. .................... 604/500 |

FOREIGN PATENT DOCUMENTS

| | | |
|---|---|---|
| WO | 0232318 | 4/2002 |
| WO | 03066147 | 8/2003 |
| WO | 2005077266 | 8/2005 |
| WO | 2006116310 | 2/2006 |
| WO | 2008023193 | 2/2008 |
| WO | 2008054448 | 5/2008 |
| WO | 2009062061 | 5/2009 |
| WO | 2009120953 | 10/2009 |
| WO | 2009139764 | 11/2009 |

* cited by examiner

METHOD AND APPARATUS FOR DELIVERING A LEAD TO A HEART

CROSS-REFERENCE TO RELATED APPLICATIONS

This application claims the benefit of and priority to U.S. Provisional Application Ser. No. 61/370,129, filed Aug. 3, 2010, entitled "Method and Apparatus for Delivering a Lead to the Heart", the contents of which are incorporated by reference herein in its entirety.

FIELD

The invention relates generally to a medical device and more particularly to a method and apparatus to deliver a device, a drug, a biologic or a substance to the heart of a patient.

BACKGROUND

The heart is surrounded by the pericardial sac, a loose layer of tissue, which may be visualized and retracted from the heart in an open chest. Retracting the pericardial sac from the heart creates the pericardial space, a space between the heart and the pericardial sac. U.S. Pat. No. 6,162,195 issued to Igo, et al. describes the pericardial sac as surrounding the heart like a glove enfolds a hand, and the pericardial space as naturally fluid-filled. The normal pericardium functions to prevent dilatation of the chambers of the heart, lubricates the surfaces of the heart, and maintains the heart in a fixed geometric position. The normal pericardial space is small in volume and the fluid film within it is too thin to functionally separate the heart from the pericardium. See Shabetai R: Pericardial and cardiac pressure, Circulation 77:1, 1988

Many cardiac surgical procedures invade the pericardial sac leaving it torn with no detrimental effect. Various approaches may be used to access the pericardial sac and the outside of the heart including a median sternotomy, a thoracotomy, a thoracoscope, a sub-xiphoid route and a transvenous route. The median sternotomy is a chest surgical technique using an incision of the skin and sternum between the xiphoid process and the suprasternal notch. The thoracotomy is a chest surgical technique using an incision of the chest wall and may include removal of a portion of a rib. The thoracoscope approach generally involves three puncture wounds to the chest, placement of ports for access with light, camera and instruments. The sub-xiphoid route uses a puncture inferior to the xiphoid process and the xiphoid process may or may not be removed. Transvenous approaches to the outside of the heart generally involve venous access on the right side of the heart and a puncture through the right atrium, right atrial appendage or superior vena cava.

Access to the outside of the heart may be useful for revising the circulation of the heart as in coronary artery bypass grafting (CABG), the delivery of pharmaceutical agents, the revision of the heart structure in support of cardiac valvular function, the placement of electrodes for pacing, sensing, monitoring, cardioverting or defibrillating, the ablation of tissue for the prevention of arrhythmias, or other structural modification. Implantable stimulation of the heart has been in clinical use since the early 1960's when electrodes were implanted on the outside of the heart, the epicardium. Insulated wires connecting the electrodes to an implantable pulse generator called "leads" were implanted by a surgical procedure.

Approaches that involve an intact chest such as the sub-xiphoid do not provide space for accessing and retracting the pericardial sac. To access the outside of the heart without unintentional perforation, incision or damage to the heart requires retraction of the pericardial sac. U.S. Pat. No. 6,315,774 issued to Daniel et al. discloses a thoracoscopic approach to access the space around the heart by the use of a pair of graspers and scissors, then grabbing and opening the pericardial sac by making a stem to stern type of incision. The pericardial sac is pulled away from the heart and may be suspended.

U.S. Pat. No. 7,597,698 issued to Chin describes creating an opening through a pericardial reflection, a fold in the pericardium but is quick to point out that dissection is hazardous because of important large blood vessels in the vicinity of the reflection. Grasping and forming a hole in the superior vena cava, for example, would be disastrous. U.S. Pat. Nos. 4,181,123 and 4,319,562 to Crosby, and 5,033,477 to Chin et al. disclose methods for placing electrodes in contact with the heart muscles from within the pericardial space without the need for thoracotomy via a sub-xiphoid route which involves penetrating the chest wall below the xiphoid process. However, Waxman, in U.S. Pat. No. 5,968,010, describes the sub-xiphoid route as so small that it is difficult to penetrate the sac without also puncturing, and thereby, damaging the heart itself. U.S. Pat. No. 4,991,578 issued to Cohen discloses distending the pericardium from the heart by injecting a small volume of fluid into the pericardium, puncturing the pericardium with a needle, passing a guide wire through the needle into the pericardium and then removing the needle. Adding fluid between the beating heart and the pericardial sac decreases the volume to which the heart may fill. Caution must be taken to avoid the extreme of this situation called tamponade in which the output of the heart is so restricted that systemic circulation is impaired.

U.S. Pat. No. 6,237,605 issued to Vaska, et al. describes devices and methods that may be utilized through a small access port in the chest, preferably through a subxiphoid penetration, and positioned within the pericardium and around the pulmonary veins without cutting or puncturing the pericardial reflections.

Cryogenic techniques applied to the heart demonstrate reversible changes to the myocardium. U.S. Pat. No. 5,733,280 issued to Avitall describes the cooling of cardiac cells and rewarming the tissue resulting in total recovery of the tissue without damage. U.S. Pat. No. 5,147,355 issued to Friedman, et al. discloses a catheter having a fluid flow passage for directing a flow of cryogenic fluid to the tip of the catheter.

Stabilization with devices applied to a beating heart is recognized in U.S. Pat. No. 6,960,205 issued to Jahns, et al., incorporated herein in its entirety by reference, describing devices that use vacuum or suction force to hold tissue. Apparatus for visualization and access is described in U.S. Pub. No. 2007/0293724 to SAADAT, et al. wherein tissue can be engaged using a vacuum or a cryo-probe. Creation of an ice-ball at the catheter tip that stabilizes the tip relative to a tissue is described in U.S. Pub. No. 2007/0116921 by Sherman, et al.

The use of suction for accessing an anatomical space of the body, and particularly for penetrating the epicardium to access pericardial space and the epicardial surface of the heart is described in U.S. Pat. No. 6,890,295 issued to Michels et al., incorporated herein in its entirety by reference. The use of suction requires a relatively large diameter apparatus to achieve sufficient retention force applied to the pericardial surface as compared to the diameter of cardiac rhythm leads.

U.S. Pat. No. 3,737,579 issued to Bolduc, incorporated herein in its entirety by reference, describes electrical leads for myocardial implantation with a rigid helix on the distal end of the lead serving as an electrode screwed into body tissue. U.S. Pat. No. 4,142,530 issued to Wittkampf, describes the screw-in type of electrode as requiring sufficient room to approach the heart wall from a direction that is more of less normal or perpendicular to the surface to allow the helix to be screwed into the heart muscle.

For applications where it is desired to access the epicardial surface of the heart, what is needed is a procedure that does not have significant morbidity, does not compromise the patient during the procedure, only requires a small wound and carries little risk of perforating the heart or other major blood vessels.

SUMMARY

Creating and accessing the pericardial space, that is, the space between the heart and the pericardial sac, is useful for delivering a device, delivering a drug, delivering a biologic, removing fluid or making a measurement. Exemplary embodiments described herein provide a small diameter device, allowing the puncture wound to be small and facilitating introduction and manipulation of the device to and within the pericardial space of a patient. The exemplary embodiments utilize cryoadhesion to adhere to the pericardial sac and manipulation of a catheter to create a tent like structure with the pericardial sac.

DETAILED DESCRIPTION

Figure 1:
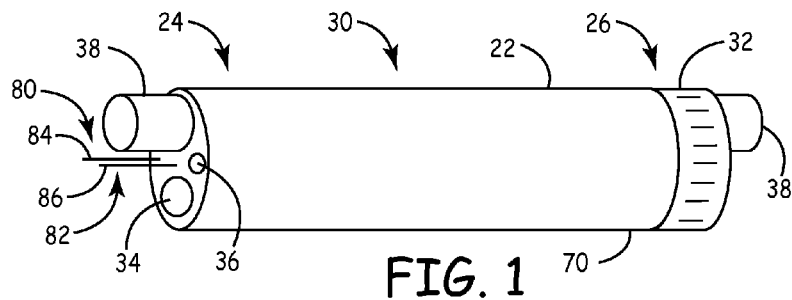
FIG. 1 is an oblique view of a catheter with an instrument in the catheter.

FIG. 1 shows catheter 30, having a catheter wall 22 that defines an elongated tube 70, and having a catheter proximal end 24 and a catheter distal end 26. At the catheter distal end is a cryoadhesion member 32. Cryoadhesion member 32 is attached to catheter wall 22 and supported by catheter 30. In this embodiment, an instrument 38 is within a catheter delivery lumen 28 (see FIGS. 2-5) and protrudes beyond catheter proximal end 24 and catheter distal end 26. First coolant lumen 34 and second coolant lumen 36 extend the length of catheter 30. First and second coolant lumens 34, 36 open at the proximal end of the catheter. Catheter 30 may be constructed of various rubbers or elastomers, silicone, urethane or the like. The catheter is longitudinally flexible yet can transmit torque through its length.

Figure 2:
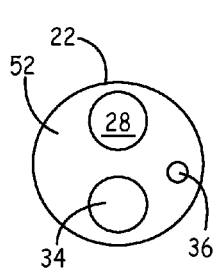
FIG. 2 is a view of the proximal end of the catheter in FIG. 1.
Figure 3:
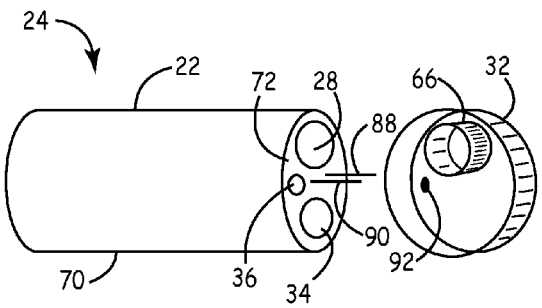
FIG. 3 is an oblique view of an elongated tube in FIG. 1.
Figure 5:
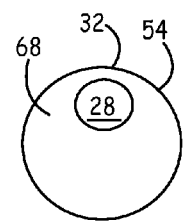
FIG. 5 is a view of the distal end view of the catheter in FIG. 1.

Delivery lumen 28 is shown in FIG. 2. Delivery lumen 28 and coolant lumens 34, 36 extend from their respective openings at the proximal end to the distal end openings of elongated tube 70 (FIG. 3) at elongated tube distal face 72. Coolant lumens 34, 36 are used to circulate a coolant such as nitrogen, nitrous oxide, or any gas or liquid that is biologically compatible. FIG. 5 shows the distal end view of catheter 30, delivery lumen 28, cryoadhesion member outer surface 68, and catheter delivery lumen end opening 54.

Figure 4:
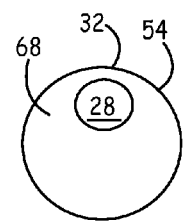
FIG. 4 is an oblique view of a cryoadhesion member in FIG. 1.

FIG. 4 shows cryoadhesion member 32 prior to attachment to catheter wall 22 forming catheter 30. Cryoadhesion member 32 incorporates sleeve 66 that forms the distal end of delivery lumen 28 after cryoadhesion member 32 is aligned and mated to elongated tube 70 of catheter 30. Sleeve 66 mates with the delivery lumen 28 such that delivery lumen 28 is continuous and uninterrupted from the proximal end of catheter 30 to the distal end of cryoadhesion member 32. Coolant lumens 34, 36 extend from the proximal end of elongated tube 70 to the distal end of elongated tube 70. To refrigerate cryoadhesion member 32, coolant is circulated through first coolant lumen 36 to cryoadhesion member 32, through cryoadhesion member 32 and is exhausted through second coolant lumen 34. The alignment and mating of delivery lumen 28 and sleeve 66 allows delivery lumen 28 to be continuous from the proximal end of catheter 30 to the distal end of cryoadhesion member 32 and prevents coolant that is circulating in cryoadhesion member 32 from entering delivery lumen 28. The interior of cryoadhesion member 32 defines a space for circulation of the coolant, the space defined by distal face 72 of elongated tube 70 and the interior of cryoadhesion member 32 minus the volume encompassed by sleeve 66.

Figure 6:
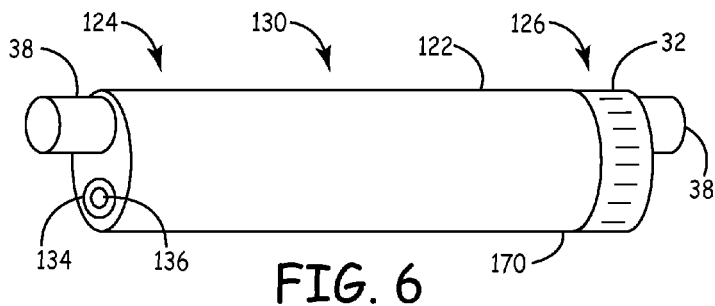
FIG. 6 is an oblique view of a second catheter.

FIG. 6 shows catheter 130, an alternative embodiment that is similar to catheter 30 wherein, catheter wall 122 corresponds to catheter wall 22, elongated tube 170 corresponds to elongated tube 70, face 172 (FIG. 8) to face 72, delivery lumen 128 corresponds to delivery lumen 28, coolant lumen 134 corresponds to coolant lumen 34 and cryoadhesion member 32 is incorporated in both embodiments. Coolant lumen 136 lies within coolant lumen 134 in catheter 130, whereas, in catheter 30, neither coolant lumen encompasses the other. As shown in FIGS. 7-10, coolant lumen 136 is shown as being concentric within coolant lumen 134 but need not be concentric.

Another embodiment (not shown) utilizes only two lumens in the catheter, wherein, a coolant lumen supports the introduction of the instrument. As the coolant lumen allows the instrument to penetrate the distal end of the catheter, a seal is required to retain coolant within the catheter and not permit coolant to escape within the body of the patient.

Circulation of coolant through the smaller of the two coolant lumens allows the advantage of the Joule-Thompson effect wherein a gas or fluid delivered to a diverging cross-sectional volume cools the gas or fluid, thus aiding refrigeration of the cryoadhesion member. The embodiment of catheter 130 corresponds to the elements and construction of the embodiment of catheter 30 with the exception of coolant lumens 36, 136. References and descriptions below will be made with respect to the embodiment of catheter 30, however, the embodiment of catheter 130 is equally applicable and the description is not limited to one embodiment or the other.

Figure 7:
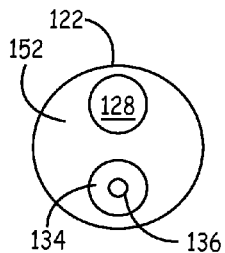
FIG. 7 is a view of the proximal end of the catheter in FIG. 6.
Figure 8:
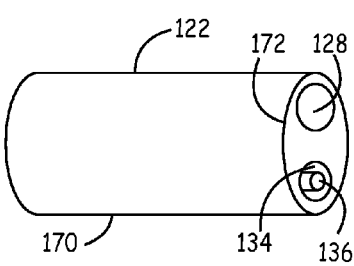
FIG. 8 is an oblique view of an elongated tube from FIG. 6.
Figure 9:
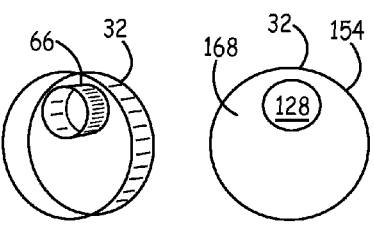
FIG. 9 is an oblique view of a cryoadhesion member in FIG. 6.
Figure 10:
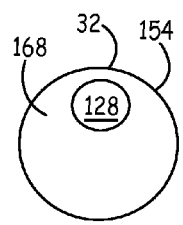
FIG. 10 is a view of the distal end of the catheter in FIG. 6.

The proximal end of catheter 130 is shown in FIG. 7. Catheter wall 122 encompasses delivery lumen 128, catheter proximal end opening 152 as well as coolant lumens 134, 136. The distal end of catheter 130 is shown in FIG. 10 and corresponds to FIG. 5, described above. Cryoadhesion member 32 is utilized for the embodiments of FIGS. 1, 6.

The relative sizes of the three lumens, delivery lumen 28, second coolant lumen 34 and first coolant lumen 36 were chosen for illustrative purposes are not necessarily to scale. The relative sizes, positions and shapes of the three lumens may vary from the illustrations. Second coolant lumen 34 or second coolant lumen 134 may be a tube or a hypotube constructed of a polymer having sufficient flexibility and strength. Cryoadhesion member 32 may be tapered, chamfered or have a variety of shapes and surface constructions to facilitate the delivery and the retention of tissue during cryoadhesion.

Cryoadhesion member 32 may be constructed of a metal such as platinum, gold, silver, or the like. Cryoadhesion member outer surface 68 may be solid metal, may be plated metal or may be metal filars. When cooled or refrigerated to a temperature of zero degrees Celsius (0° C.), the metal outer surface 68 will freeze to and adhere to a tissue. When cooled to a temperature of about minus 30 degrees Celsius, the tissue will adhere firmly to the cryoadhesion member yet, will recover following warming. A temperature of minus 30 degrees Celsius is utilized for mapping during procedures for the endocardial ablation of cardiac tissue. While there are reports of the use of minus 32 degrees Celsius for mapping, the location of the temperature measurement sensor, commonly a thermocouple, relative to warm, perfused tissue may induce measurement variation due to large temperature gradients. At this temperature, cardiac tissue will recover when warmed; colder temperatures are used to injure tissue for therapeutic purposes.

A thermocouple 92 may be placed in cryoadhesion member 32 to measure the temperature of the member; regulation of the member's temperature may be based on the temperature measured by the thermocouple. The use of a thermocouple inside a metallic element on a catheter is well known in the art and is not further described here. The thermocouple may be electrically coupled to the proximal end of the catheter by use of insulated conductors 80, 82 routed on the outside of catheter wall 22, in delivery lumen 28, in one of coolant lumens 34, 36 or otherwise within catheter wall 22. Conductors 80, 82 have proximal ends 84, 86 and distal ends 88, 90, respectively. Conductor distal ends 88, 90 are joined on cryoadhesion member 32 to form thermocouple 92.

Figure 11:
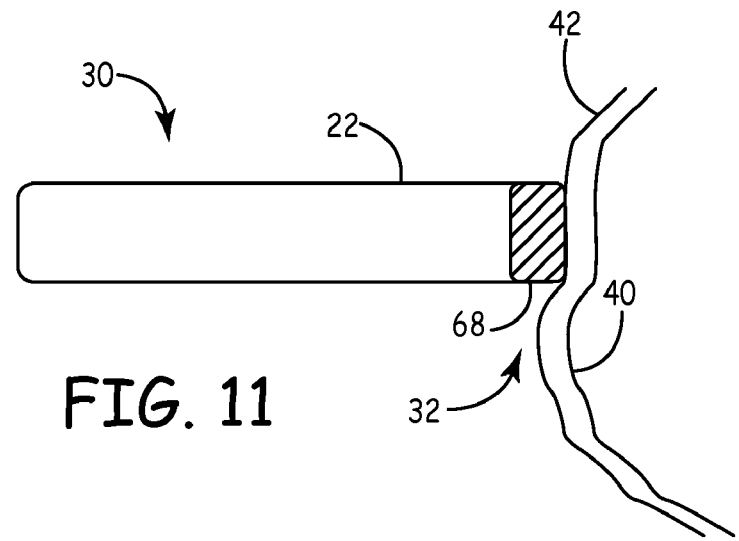
FIG. 11 is a conceptual illustration of a catheter, the pericardial sac (cross-section) and the heart (cross-section where the cryoadhesion member on the end of the catheter is touching the pericardial sac.

FIG. 11 shows catheter 30, cryoadhesion member 32, and cryoadhesion member outer surface 68 in contact with a pericardial sac, outer tissue 42. The heart, inner tissue 40, is illustrated to the right of outer tissue 42. The heart is illustrated conceptually as a cross-section of a portion of the heart. While the heart of a patient is beating and moving, this illustration captures the heart, inner tissue 40, in a static, cross-sectional view. The pericardial sac, outer tissue 42 is shown in close proximity to the heart.

Figure 12:
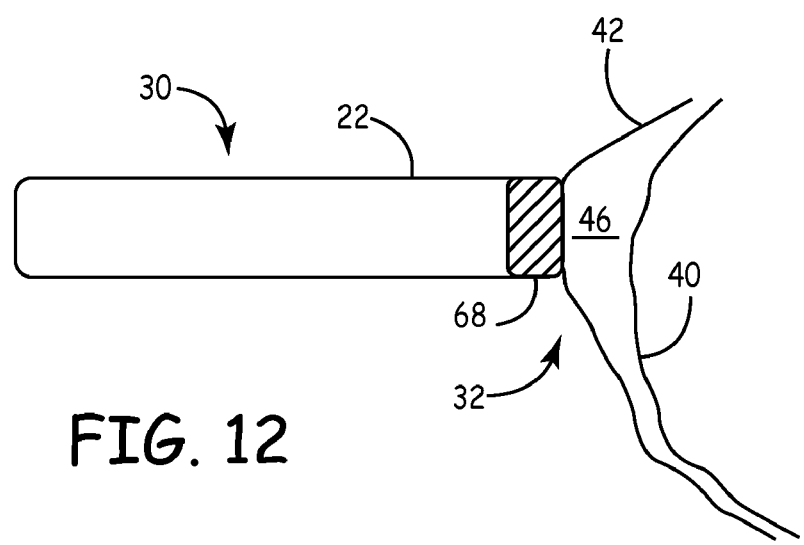
FIG. 12 is a conceptual illustration of a catheter, the pericardial sac (cross-section) and the heart (cross-section) where the cryoadhesion member has been adhered to the pericardial sac and has been manipulated to form an anatomic space between the pericardial sac and the heart.

Moving to FIG. 12, cryoadhesion member 32 has been refrigerated and is adhering to the pericardial sac, outer tissue 42. Catheter 30 has been manipulated to create anatomic space 46 between the heart, inner tissue 40, and the pericardial sac, outer tissue 42. The manipulation of catheter 30 may be as simple as retraction once it is cryoadhered to outer tissue 42. Alternatively, or in addition, manipulation may be achieved by placing a curved stiffening member within catheter 30, likely within delivery lumen 28. A stylet is a stiffening member which may be curved. Stylets are commonly used for the implantation of cardiac rhythm leads such as are used for cardiac pacing and cardiac defibrillation. A catheter manipulating element such as a pull wire, a push wire, a lever, a cam, a cable or the like may be utilized to deflect catheter 30. The use of retraction alone or on combination with mechanically directed deflection constitutes manipulation of catheter 30. Anatomic space 46 created between the heart and the pericardial sac is known as the pericardial space. The manipulation to create anatomic space 46 may be retraction. As catheter 30 is retracted, outer tissue 42 pulls tissue from around other portions of the pericardial sac surrounding the heart to form a tent like structure, as illustrated in FIG. 12. In this manner, cryoadhesion member 32 has been cryoadhered to outer tissue 42 and the pericardial sac, outer tissue 42, has been tented.

Figure 13:
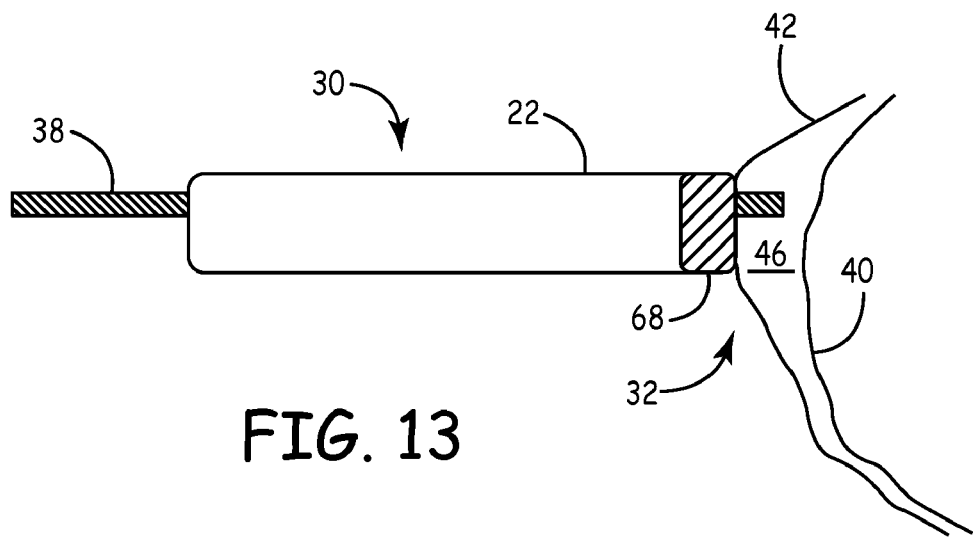
FIG. 13 is a conceptual illustration of a catheter, an instrument, the pericardial sac (cross-section) and the heart (cross-section) where the instrument is within the catheter and the instrument protrudes through the pericardial sac into the anatomic space.
Figure 14:
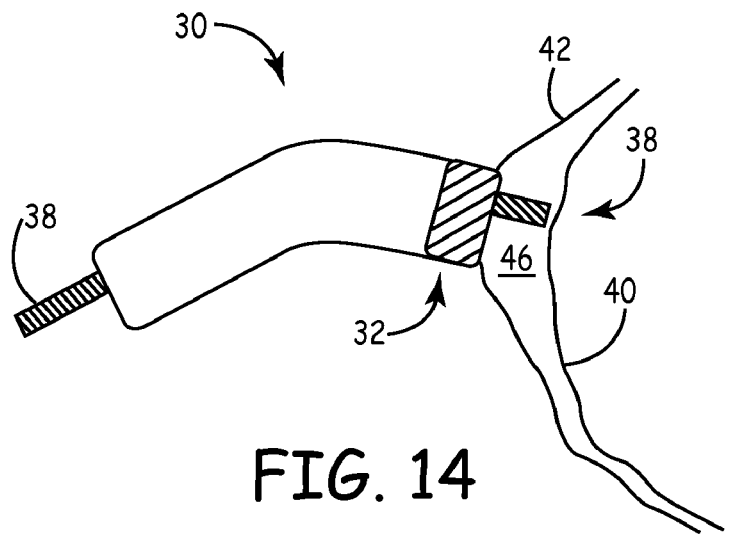
FIG. 14 is a conceptual illustration of the distal end of a catheter, the pericardial sac, the heart and an instrument.
Figure 15:
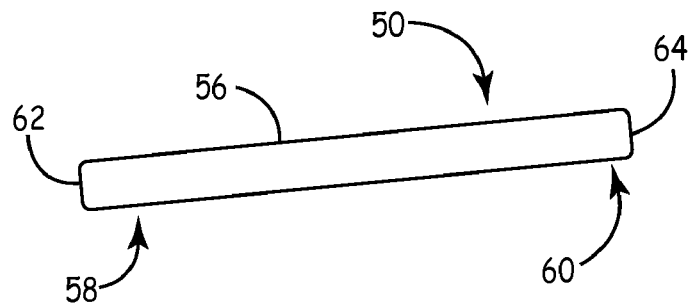
FIG. 15 is a conceptual illustration of a second catheter.
Figure 16:
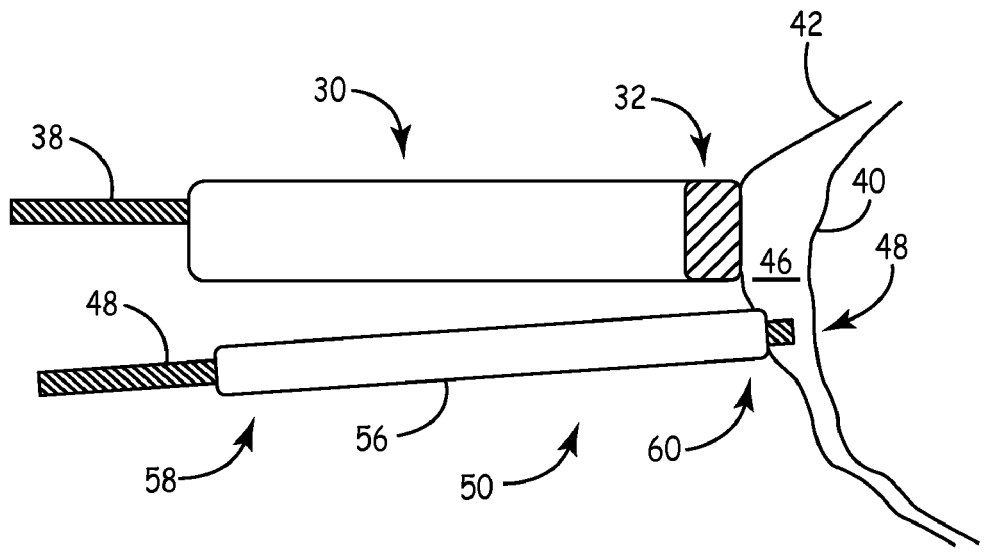
FIG. 16 is a conceptual illustration of a catheter adhered to the pericardial sac, an instrument within the catheter, second catheter and a second instrument within the catheter and protruding through the pericardial space to the anatomic space.

In FIG. 13, the catheter remains cryoadhered to outer tissue 42 as shown in FIG. 12. Instrument 38 is advanced through delivery lumen 28 to outer tissue 42. Instrument 38 may be a cardiac rhythm lead, a puncture tool system, a needle, a blade, a guide wire, a stylet, an imaging instrument, a source of light, a helix, a biopsy tool, a blunt dissection instrument or a cannula. Instrument 38 punctures the pericardial sac, outer tissue 42, thereby gaining access to anatomic space 46 while outer tissue 42 is retained tented.

After access to anatomic space 46 is obtained, delivery lumen 28 of catheter 30 may be used advantageously to perform a diagnostic measurement or deliver a substance such as a drug, a biologic or another device. If instrument 38 that punctured outer tissue 42 and was used to gain access to anatomic space 46 is a device that may be attached to the heart, instrument 38 may be advanced to inner tissue 40 and suitably installed. Instrument 38 may also be used to deliver a substance such as a drug to anatomic space 46. Another device may be delivered using instrument 38. For example, if instrument 38 were a guide wire with a distal end that is stiff enough and sharp enough to puncture outer tissue 42, following access to anatomic space 46, an over-the-wire device may be delivered through delivery lumen 28 of catheter 30 and over the guide wire. As another example, if instrument 38 were a pacing lead with a sharp, helical fixation member upon its distal end, the fixation member could be used to puncture outer tissue 42, and then instrument 38 would be advanced to the heart, inner tissue 40, and suitably attached and fixed to the heart.

Alternatively, instrument 38 may be withdrawn and another device may be placed within delivery lumen 28. Instrument 38 may be a tool that is designed for puncturing the pericardial sac, outer tissue 42. After outer tissue 42 has been punctured, instrument 38 may be withdrawn and a parameter measured. However, it may not be necessary to withdraw instrument 38 to perform a measurement. Pressure and other parameters may be measured through delivery lumen 38 of catheter 30 with instrument 38 within delivery lumen 38.

With catheter distal end 26 of catheter 30 residing in anatomic space 46, a fluid or other substance may be introduced. The substance may be a drug, a solution or a biologic. Another option is to apply suction to catheter delivery lumen 28 to remove blood or other fluid such as might be encountered with a pericardial effusion or tamponade.

With access to anatomic space 46, catheter 30 is particularly suited for delivery of devices to the heart, to the outside, to the outside and into, and to the outside and through the heart. For example, cardiac leads may be delivered for transmural lead implantation, placing a pacing lead or a high voltage defibrillation lead or a similar device with a sensor in the heart wall. An ablation of tissue for beneficial therapeutic benefit may be accomplished by advancing an ablation device through delivery lumen 28 of catheter 30 and manipulating the device to a targeted location on the heart.

While retaining outer tissue 42 tented, instrument 38 may be further advanced to the heart, inner tissue, 40. Prior to or during the process of advancing instrument 38, catheter 30 may be deflected. When advancing an instrument to the heart through delivery lumen 28 of catheter 30, the instrument may approach the surface of the heart tangentially as illustrated in FIG. 13. By manipulating catheter 30, as described above, and specifically, deflecting catheter 30, catheter 30 may be oriented so an instrument emerging from the distal end of catheter 30 will approach the heart so the instrument is normal to the surface of the heart. If not precisely normal, the approach to the heart can be closer to normal that if the catheter had not been deflected. Providing a normal approach may allow engagement of instrument 38 with the heart that, otherwise, may not have resulted in proper engagement.

Warming of cryoadhesion member 32 serves to disable the cryoadhesion and release outer tissue 42. Warming may be accomplished by circulating coolant that has been warmed above zero degrees Celsius, circulating coolant that is at normal body temperature of about plus 37 degrees Celsius or simply stopping the circulation of coolant and allowing the warming of the tissue from the surrounding tissues and fluids. After warming and withdrawing the instrument or other tool that has been used, devices that have been affixed to the heart, inner tissue 40, remain in place. If tethered, the tether remains threaded through the opening that was generated in the pericardial sac, outer tissue 42, while gaining access to the pericardial space, anatomic space 46.

The use of cryoadhesion allows a relatively small diameter device to adhere to the pericardial sac and to tent the sac, thereby creating anatomic space 46. The small diameter device corresponds to a small surgical puncture wound in the patient having cosmetic benefit and less morbidity than might be encountered with a larger wound. Suction may be applied in combination with cryoadhesion to gather up the pericardial sac, outer tissue 42, and to then apply cryoadhesion. Such a procedure may be useful in the event that cryoadhesion adheres the cryoadhesion member outer surface 68 to both the pericardial sac, outer tissue 42, and the heart, inner tissue 40.

Retracting or deflecting cryoadhesion member 32 to tent and create anatomic space 46 stabilizes outer tissue 42. While inner tissue 40, the heart, is moving by virtue of beating, catheter 30 and cryoadhesion member 32 are stable due to physical interferences of the access through the body of the patient and at the hands of the physician user. Once punctured, outer tissue 42 remains cryoadhered to cryoadhesion member 32 and, therefore, stabilized while the heart beats.

The use of cryoadhesion allows relatively quick adherence to outer tissue 42 and adjustment of the cryoadhesion by controlling the temperature of cryoadhesion member 32 to create and access anatomic space 46.

Thus, embodiments of the invention are disclosed. One skilled in the art will appreciate that the present invention can be practiced with embodiments other than those disclosed. The disclosed embodiments are presented for purposes of illustration and not limitation, and the present invention is limited only by the claims that follow.

We claim:

1. A method for creating and accessing an anatomic space within a body and between an inner tissue and an outer tissue that are in close proximity to each other comprising the steps of:
    applying a distal end of a catheter against the outer tissue, the catheter comprising a catheter wall extending between a catheter proximal end and a cryoadhesion member, the catheter wall supporting the cryoadhesion member at the distal end of the catheter, and surrounding a catheter delivery lumen extending between a catheter delivery lumen proximal end opening and a cryoadhesion member distal end opening, the catheter wall surrounding a coolant lumen for circulating coolant to the cryoadhesion member, the coolant lumen extending between the catheter proximal end and the cryoadhesion member, the coolant lumen fluidly coupled to the cryoadhesion member;
    cryoadhering an outer surface of the cryoadhesion member to the outer tissue by contacting the outer tissue with the cryoadhesion member, and
        refrigerating the cryoadhesion member with coolant circulated through the coolant lumen;
    manipulating the catheter distal end to tent the outer tissue to create the anatomic space between the inner tissue and the outer tissue;
    introducing a first instrument through the catheter delivery lumen proximal end opening;
    advancing the first instrument through the catheter delivery lumen to the cryoadhesion member distal end opening and to the outer tissue; and
    penetrating the outer tissue with the first instrument to access the anatomic space while the refrigerated cryoadhesion member stabilizes the outer tissue.

2. The method of claim 1 further comprising the step of applying suction to the catheter delivery lumen proximal end opening.

3. The method of claim 1 wherein the cryoadhesion member is refrigerated to a temperature of less than 0 degrees Celsius.

4. The method of claim 1, wherein the cryoadhesion member is refrigerated to a temperature of about minus 30 degrees Celsius.

5. The method of claim 1, wherein the cryoadhesion member is refrigerated to a temperature of minus 32 degrees Celsius.

6. The method of claim 1 wherein the catheter further comprises a thermocouple disposed on the cryoadhesion member which is electrically coupled to the proximal end of the catheter.

7. The method of claim 1 wherein the first instrument is one of:
    a cardiac rhythm lead, a puncture tool system, a needle, a blade, a guide wire, a stylet, an imaging instrument, a source of light, a helix, a biopsy tool, a blunt dissection instrument and a cannula.

8. The method of claim 1, further comprising the step of:
measuring a parameter or introducing a fluid, a substance, a drug, a biologic or a device through the catheter delivery lumen.

9. The method of claim 1, further comprising the steps of:
incorporating a catheter manipulating element extending between the catheter distal end and the catheter proximal end, the catheter manipulating element having an element distal end and an element proximal end, and
coupling the catheter manipulating element distal end to the catheter distal end, wherein manipulating the catheter manipulating proximal end causes the distal end of the catheter to deflect.

10. The method of claim 9, further comprising the step of deflecting the catheter; and
advancing the first instrument to the inner tissue, wherein, the first instrument approaches the inner tissue more near normal to the inner tissue than were the catheter not deflected.

11. The method of claim 1, further comprising the steps of:
applying a distal end of a second catheter against the tented outer tissue, the second catheter having a second catheter wall extending between a second catheter proximal end and the second catheter distal end and surrounding a second catheter lumen extending between a second catheter lumen proximal end opening and a second catheter lumen distal end opening;
introducing a second instrument through the second catheter lumen proximal end opening;
advancing the second instrument through the second catheter lumen to the second catheter lumen distal end opening and to the outer tissue; and
puncturing the outer tissue with the second instrument, thereby accessing the created anatomic space between the inner tissue and the outer tissue.

12. The method of claim 11, wherein the second instrument is one of a cardiac rhythm lead, a puncture tool system, a needle, a blade, a guide wire, a stylet, an imaging instrument, a source of light, a helix, a biopsy tool, a blunt dissection instrument and a cannula.

13. The method of claim 11, further comprising the step of:
measuring a parameter or introducing a fluid, a substance, a drug or a device through the second catheter lumen.

14. The method of claim 11 further comprising the step of:
applying suction to the second catheter lumen proximal end opening.

15. A system for creating and accessing an anatomic space within a body and between an inner tissue and an outer tissue that are in close proximity to each other comprising:
a catheter, the catheter comprising a catheter wall that extends between a catheter proximal end and a catheter distal end;
a cryoadhesion member attached to the distal end of the catheter wall;
a catheter delivery lumen that extends between a catheter delivery lumen proximal end opening and a cryoadhesion member distal end opening;
a first coolant lumen and a second coolant lumen, wherein:
the first and second coolant lumens extend between the catheter proximal end and the cryoadhesion member on the catheter distal end;
the first and second coolant lumens are in fluid communication with the cryoadhesion member;
the first coolant lumen receives coolant at the proximal end of the catheter and communicates the coolant to the cryoadhesion member; and
the second coolant lumen receives the coolant from the cryoadhesion member and exhausts the coolant at the proximal end of the catheter;
and
a first instrument delivered within the catheter delivery lumen.

* * * * *